United States Patent
Eutick

(10) Patent No.: US 10,493,099 B2
(45) Date of Patent: Dec. 3, 2019

(54) COMPOSITIONS CONTAINING ARSENIC AND THEIR USE IN METHODS OF TREATMENT

(71) Applicant: Eupharma Pty Ltd, Northbridge, New South Wales (AU)

(72) Inventor: Malvin Eutick, Northbridge (AU)

(73) Assignee: EUPHARMA PTY LTD, Northbridge, New South Wales (AU)

( * ) Notice: Subject to any disclaimer, the term of this patent is extended or adjusted under 35 U.S.C. 154(b) by 0 days.

(21) Appl. No.: 15/547,102

(22) PCT Filed: Jan. 29, 2016

(86) PCT No.: PCT/AU2016/050046
§ 371 (c)(1),
(2) Date: Jul. 28, 2017

(87) PCT Pub. No.: WO2016/119019
PCT Pub. Date: Aug. 4, 2016

(65) Prior Publication Data
US 2017/0354680 A1    Dec. 14, 2017

(30) Foreign Application Priority Data
Jan. 29, 2015    (AU) ................................ 2015900258

(51) Int. Cl.
| | | |
|---|---|---|
| *A61K 33/36* | (2006.01) | |
| *C01G 28/00* | (2006.01) | |
| *A61K 9/48* | (2006.01) | |
| *A61K 9/00* | (2006.01) | |

(52) U.S. Cl.
CPC ............. *A61K 33/36* (2013.01); *A61K 9/0053* (2013.01); *A61K 9/4825* (2013.01); *A61K 9/4858* (2013.01); *A61K 9/4866* (2013.01); *C01G 28/002* (2013.01)

(58) Field of Classification Search
CPC ................................ A61K 33/36; C01G 28/00
See application file for complete search history.

(56) References Cited

PUBLICATIONS

Han, M.J., et al., Direct evidence of arsenic(III)-carbonate complexes obtained using electrochemical scanning tunneling microscopy, Analytical Chemistry, 2007, vol. 79, No. 10, pp. 3615-3622 (NPL cite. No. 7, Jul. 28, 2017 IDS).*
Shliakhov, [Use of arsenous carbonate waters in patients with ischemic heart disease undergoing sanatorium treatment], Voprosy kurortologii, fizioterapii, i lechebnoi fizicheskoi kultury, (May-Jun. 1986) No. 3, pp. 61-62. (Record 9 of 37 in search results.).*
Partial written translation of Shliakhov ([Use of arsenous carbonate waters in patients with ischemic heart disease undergoing sanatorium treatment], Voprosy kurortologii, fizioterapii, i lechebnoi fizicheskoi kultury, (May-Jun. 1986) No. 3, pp. 61-62) obtained from the Translations Branch, USPTO.*
International Search Report and Written Opinion, PCT/AU2016/050046, dated Mar. 1, 2016.
Chen S-J et al. From an old remedy to a magic bullet: molecular mechanisms underlying the therapeutic effects of arsenic in fighting leukemia. Blood. Jun. 16, 2011; 117(24): 6425-6437.
Gibaud S and Jaouen G. Arsenic-based drugs: from Fowler's solution to modern anticancer chemotherapy. Topics in Organometallic Chemistry. 2010; 32: 1-20.
Zhu M-J et al. How acute promyelocytic leukaemia revived arsenic. Nature Reviews. Sep. 2002; 2(9): Nature Reviews Cancer. Sep. 2002; 2(9): 705-714.
Antman KH. Introduction: the history pf arsenic trioxide in cancer therapy. The Oncologist. 2001; 6(suppl 2): 1-2.
Thomas X and Troncy J. Arsenic: a beneficial therapeutic poison—a historical overview. Adler Museum Bulletin. Jun. 2009; 35(1): 3-13.
Han M-J et al. Direct evidence of arsenic(III)—carbonate complexes obtained using electrochemical scanning tunneling microscopy. Analytical Chemistry. May 2007; 79(10): 3615-3622.

* cited by examiner

*Primary Examiner* — H. Sarah Park
(74) *Attorney, Agent, or Firm* — Myers Bigel, P.A.

(57) ABSTRACT

A pharmaceutical composition is provided comprising a highly soluble arsenic carbonate and/or bicarbonate compound and which is useful in the treatment of a variety of cancers, including acute promyelocytic leukaemia. The arsenic carbonate and/or bicarbonate salt acts as a solid, and so orally deliverable, improved bioequivalent delivery form of arsenic trioxide IV solutions.

19 Claims, 5 Drawing Sheets

COMPOSITIONS CONTAINING ARSENIC AND THEIR USE IN METHODS OF TREATMENT

RELATED APPLICATIONS

This application is a 35 U.S.C. § 371 national phase entry of PCT Application PCT/AU2016/050046, filed Jan. 29, 2016, and published in English on Aug. 4, 2016, as International Publication No. WO 2016/119019, and which claims the benefit of Australian Application No. 2015900258, filed Jan. 29, 2015, the disclosure of each of which is incorporated herein by reference in its entirety.

FIELD OF THE INVENTION

The invention relates to the fields of pharmaceutical formulation and medical treatment of cancers. More particularly, this invention relates to arsenic containing compositions and their use in the treatment of certain cancers.

BACKGROUND TO THE INVENTION

Any reference to background art herein is not to be construed as an admission that such art constitutes common general knowledge in Australia or elsewhere.

Acute promyelocytic leukaemia (APL) is a rare disease, accounting for 10-15% of all acute myelogenous leukaemia in adults. APL is characterised by the accumulation of clonal haemopoietic precursors blocked at specific stages of development. APL is classified under the French-American-British (FAB) morphological scheme as subtype M3 of acute myeloid leukaemia (AML). The bone marrow morphology is characterised by greater than 30% blasts and abnormal promyelocytes; multiple Auer bodies, heavy granulation obscuring the basophilic cytoplasm, and strong positive cytochemistry.

The disease involves a balanced translocation involving chromosomes 15 and 17 (t15:17) although exceedingly rare variants of this leukaemia show balanced translocations of chromosomes 11/17 and 5/17. As a result of these translocations APL blasts invariably synthesize aberrant fusion forms of the retinoic receptor type alpha, PML-RARα in the case of t15:17, PLZF-RARα and NPMRARα in the case of t11:17 and t5:17, respectively. In addition, the breakpoint of the t15:17 chromosomal translocation is heterogeneous, leading to at least three molecular types of PML-RARα fusion proteins. The PML/RARα fusion protein is considered to have an important role in APL pathogenesis by causing a maturation block at the promyelocyte stage of myeloid differentiation. These molecular defects allow the classification of APL patients in two categories: all-trans-retinoic acid (ATRA)-sensitive and ATRA-resistant. Patients with the t15:17 and t5:17 translocations are ATRA-sensitive, and those with the t11:17 translocation are resistant. Among other actions, this mutant protein disaggregates PML Oncogenic Domains (PODs), which are spherical nuclear bodies that are attached to the nuclear matrix. This disorganisation of the PODs is also thought to play a crucial role in APL pathogenesis by causing inhibition of apoptosis mechanisms. The t(15;17) translocation may be evidenced with reverse transcriptase-polymerase chain reaction (RTPCR) using specific PML and RARα oligonucleotides. Depending on the RT-PCR technique used, its sensitivity level may vary between $1/10^4$ and $1/10^6$ cells.

The treatment of newly diagnosed APL patients consists of two phases: an induction phase to achieve remission (defined by bone marrow clearance) and then a set of cycles of consolidation and maintenance.

All-trans retinoic acid (ATRA) coupled with the anthrocycline chemotherapy (CT) (Idarubicin; BLOOD, Vol. 120, No. 8) has been considered as the APL standard first line treatment, although recent data from Iland et al (2012) summarising the Australian Leukaemia and Lymphoma Group's (ALLG) study suggests that in first line therapy, ATRA plus CT, coupled with IV arsenic trioxide, may provide a more effective treatment protocol. Arsenic trioxide had already been established as an effective therapy for patients in a third line setting and these recent results from the ALLG study further highlight the value of arsenic trioxide as an effective treatment in APL.

Although arsenic trioxide ($As_2O_3$) is a well-known poison, it has been in medical use for a long time. In 1865, arsenic compounds, (often called Fowler's Solution which is a solution containing 1% potassium arsenite ($KAsO_2$)) was already described for the treatment of chronic myelogenous leukaemia. Because of its chronic toxicity, this treatment was replaced by the non specific alkyl sulfonate chemotherapeutic agent, busulfan in the middle of the 20th century. After a large scale clinical screening, therapeutic effects were identified in some human cancers such as leukaemia, oesophageal carcinoma, and lymphoma.

There are now a number of commercially available treatments for APL which employ arsenic trioxide as the active ingredient in the form of a sterile IV infusion and where the treatment occurs by dilution of the concentrated IV 10 mg/10 mL solution of arsenic trioxide into an infusion bag containing sterile saline or glucose and the patient given the drug given by slow infusion.

Sterile IV formulations of arsenic trioxide and their use in treating various types of leukaemia's are disclosed in U.S. Pat. No. 7,879,364 and WO2004/032822. Since arsenic trioxide is only sparingly soluble in water at physiological or acidic pH these documents describe solubilising arsenic trioxide in an aqueous solution at high pH, such as a pH greater than 12. To assist in dissolving all of the arsenic trioxide and attain a clear solution, stirring and heating are recommended. The solution thereby provided is too basic to be useful as a pharmaceutical composition and so this solution is first diluted in water, for example, to a concentration of about 1 mg/mL, pH 12. The arsenic trioxide solution is then adjusted with hydrochloric acid with constant stirring until the pH is 8.0 to 8.5. The inventors in U.S. Pat. No. 7,879,364 state that highly concentrated hydrochloric acid is not suitable as it causes precipitation. The partially neutralized arsenic trioxide solution is then sterilised and packaged.

The sterile IV formulation has a number of drawbacks. Firstly, it must be prepared (usually by hospital compounding laboratories) by aseptic addition of the 1 mg/mL solution into a sterile infusion bag. Secondly, the form of delivery is by slow infusion of the dilute IV bag, hence a patient must spend a number of hours in hospital on a considerable number of occasions during the induction and maintenance treatment phases over period of about 4 to 6 months. This is a considerable drain on the patients, their families, the hospital resources and medical staff's time.

There is therefore a need for an improved formulation to deliver an active arsenic species useful in the treatment of a number of forms of cancer.

SUMMARY OF INVENTION

According to a first aspect of the invention, there is provided a pharmaceutical composition comprising an arsenic carbonate and/or arsenic bicarbonate and a pharmaceutically acceptable excipient.

Suitably, the pharmaceutical composition comprises the arsenic carbonate and/or bicarbonate in solid form.

Preferably, the arsenic carbonate and/or bicarbonate is an arsenic (III) carbonate or bicarbonate.

In certain embodiments the arsenic carbonate and/or bicarbonate may be an alkali metal and/or an alkaline earth metal arsenic carbonate and/or bicarbonate.

In one preferred embodiment the arsenic carbonate and/or bicarbonate may be selected from the group consisting of a sodium arsenic carbonate and/or bicarbonate, a potassium arsenic carbonate and/or bicarbonate and a calcium arsenic carbonate and/or bicarbonate.

Preferably, the arsenic carbonate and/or bicarbonate is a sodium arsenic carbonate and/or bicarbonate and more preferably a sodium arsenic (III) carbonate or bicarbonate.

In one embodiment, the arsenic (III) carbonate or bicarbonate may be selected from the group consisting of $NaAs(OH)_2CO_3$, $As_2(CO_3)_3$, $As(HCO_3)_3$, $Na_2As(OH)_3CO_3$, $NaAs(CO_3)_2$, $Na_3As(CO_3)_3$, $NaAs(HCO_3)_4$, $Na_2As(HCO_3)_5$, $Na_3As(HCO_3)_6$ and closely related analogues wherein the sodium in the formulae presented is replaced with another counter ion.

The counter ion may be selected from sodium, potassium, calcium and ammonium.

Preferably, the arsenic carbonate and/or bicarbonate is an arsenic carbonate compound or salt.

According to a second aspect of the invention there is provided a method of treating a cancer in a patient including the step of orally administering an arsenic carbonate and/or bicarbonate to the patient to thereby treat the cancer.

A third aspect of the invention resides in an arsenic carbonate and/or bicarbonate for use in treating a cancer in a patient.

In certain embodiments of the second and third aspects, the arsenic carbonate and/or bicarbonate is administered in solid form.

In relation to the second and third aspects, in one embodiment the cancer is a haematological malignancy. In one embodiment the cancer is a leukaemia, multiple myeloma, a solid tumour or a lymphoma.

Preferably, the cancer is acute promyelocytic leukaemia (APL).

The arsenic carbonate and/or bicarbonate, of the second and third aspects, may be as described for the first aspect. The arsenic carbonate and/or bicarbonate may be administered as part of the pharmaceutical composition of the first aspect.

According to a fourth aspect of the invention there is provided a process for producing an arsenic carbonate and/or bicarbonate in solid form for oral delivery to a patient in need of cancer therapy including the steps of:
 (a) solubilising arsenic trioxide in a strongly basic solution;
 (b) contacting the strongly basic solution with a carbonate and/or bicarbonate compound; and
 (c) removing the solvent from the strongly basic solution containing the dissolved arsenic carbonate and/or bicarbonate compound;
to thereby produce the arsenic carbonate and/or bicarbonate in solid form.

The strongly basic solution may be a solution of at least pH 10, preferably at least pH 11, more preferably at least pH 12 and even more preferably about pH 13.

The strongly basic solution may be a solution of a hydroxide of an alkali metal and/or an alkaline earth metal or ammonium hydroxide.

A fifth aspect of the invention resides in an arsenic carbonate and/or bicarbonate in solid form when produced by the process of the fourth aspect.

A sixth aspect of the invention resides in a method of delivering a therapeutically effective amount of arsenic to a patient including the step of administering to the patient an appropriate amount of an arsenic carbonate and/or bicarbonate.

Suitably, the administration is oral administration of a solid form of arsenic carbonate and/or bicarbonate.

The method of the sixth aspect may include any of the embodiments described for the first to the fifth aspects.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Figure 1:
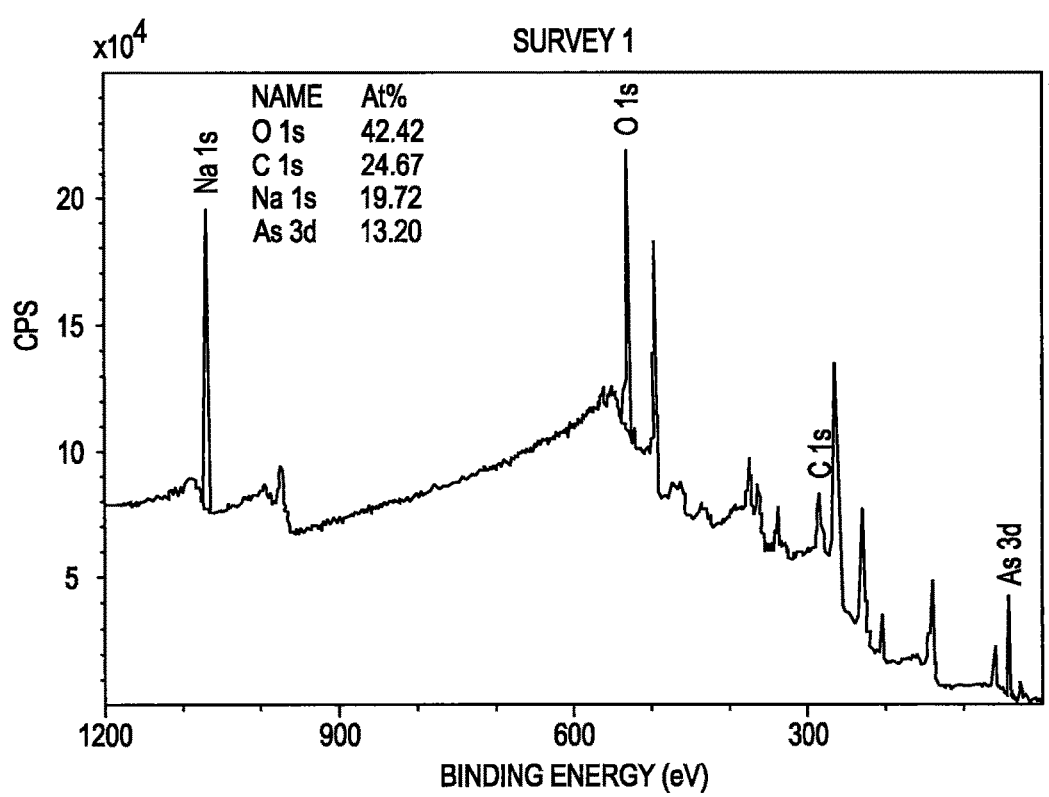
FIG. 1 is a X-ray photoelectron spectroscopy (XPS) scan of arseno carbonate AC01 as an arsenic (III) carbonate of the invention; and FIG 2A
Figure 2A:
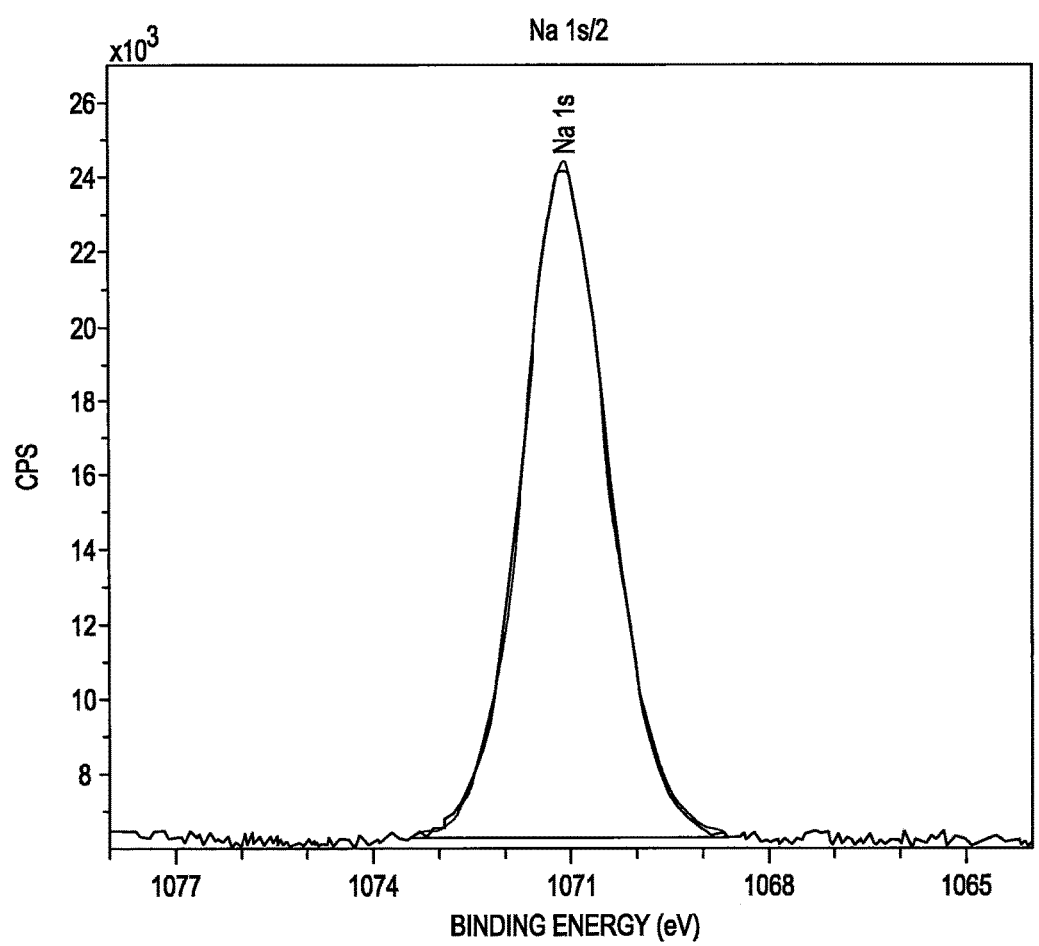
-FIG 2D is a series of high resolution images of the key peaks seen in FIG. 1.
Figure 2B:
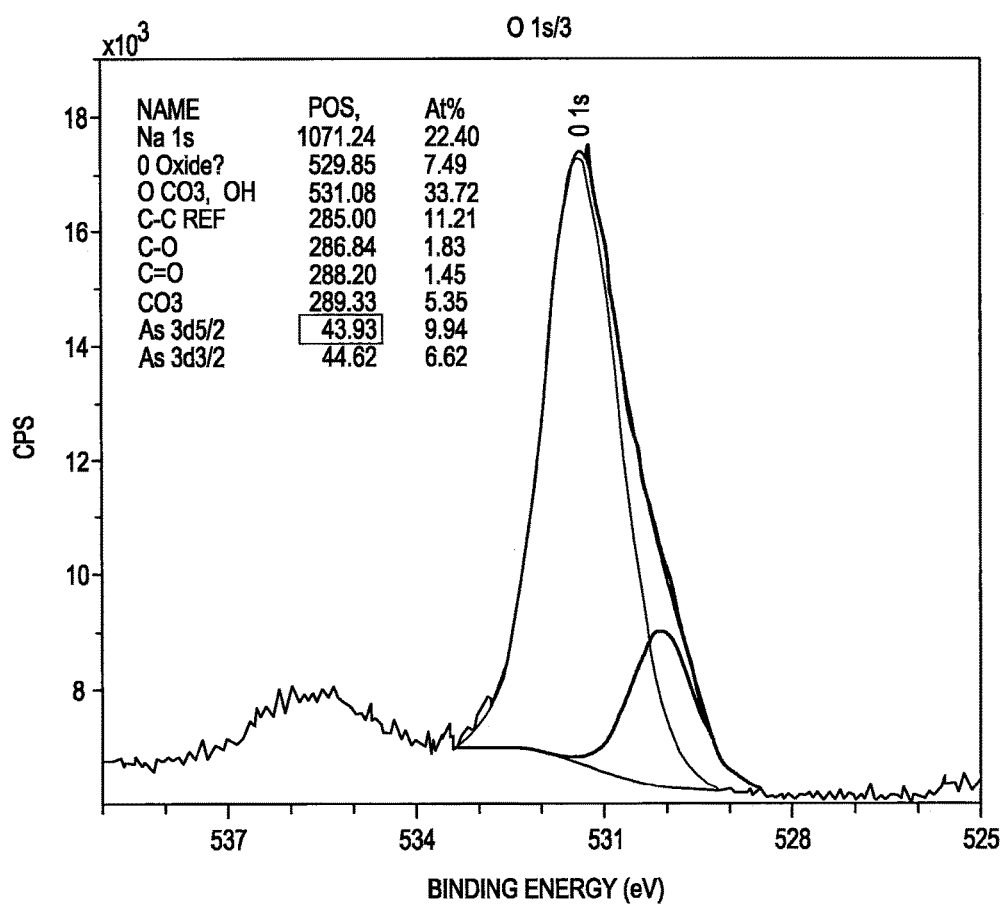
Figure 2C:
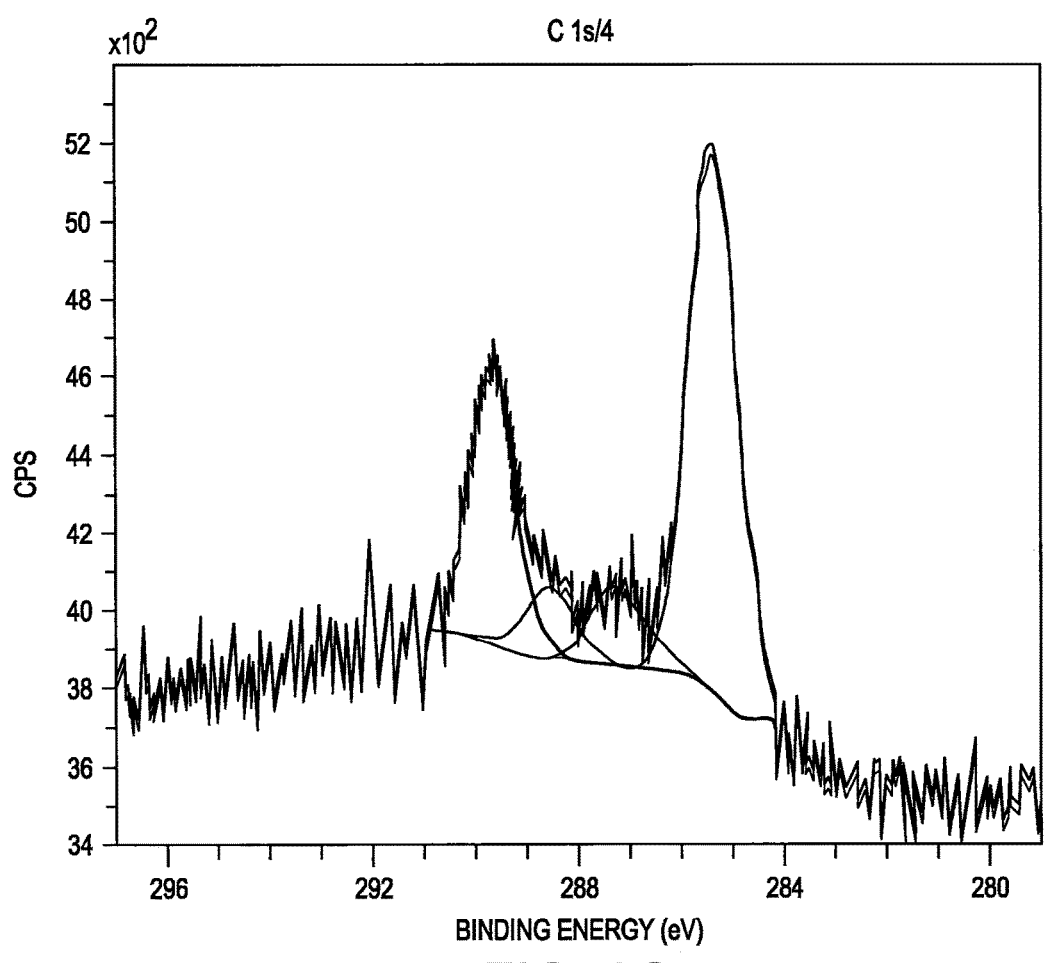
Figure 2D:
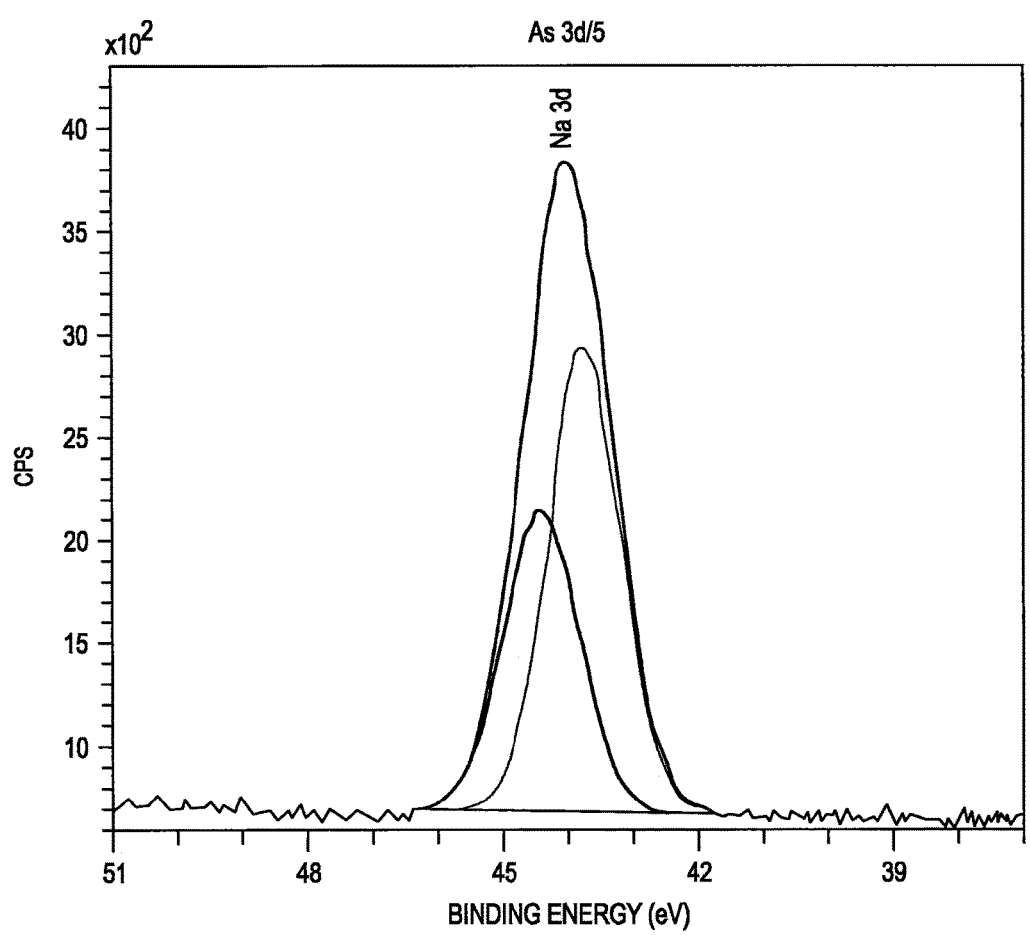

The present invention is predicated, at least in part, on the realisation that problems with the poor water solubility of arsenic trioxide and the extreme difficulty in dissolving arsenic trioxide in anything other than a very basic solution, could be overcome by forming a much more soluble arsenic carbonate and/or bicarbonate salt (preferably an arsenic III carbonate and/or bicarbonate) prior to its delivery to a patient. The typical solution to the solubility issue has been to dissolve the arsenic trioxide in a solution of sodium hydroxide and then to adjust the pH of this solution down to pH 6 to 8, to be better suited for delivery to patients in a liquid form. The use of concentrated acid has always been avoided due to concerns over the precipitation of the arsenic trioxide from solution.

The present inventor has surprisingly found that when a solution of arsenic trioxide in sodium hydroxide is dried down with a carbonate or bicarbonate compound an arsenic (III) carbonate or bicarbonate is formed which can then be very rapidly dissolved in stomach acid without any precipitation of the dissolved arsenic trioxide. This goes against conventional wisdom which teaches that the strongly acidic gastric juices should cause a precipitation of arsenic trioxide from solution almost immediately after the salt dissolves. This finding allows the oral delivery of an arsenic III ion as an effective arsenic trioxide equivalent to the sterile IV product in a convenient solid form which can be manufactured in the form of a tablet, suppository, granule or, preferably, capsule. There has been a long felt need for such a delivery option since it can greatly reduce the amount of time a patient needs to spend in hospital, particularly during the maintenance phase of treatment. This is an improvement for the patient and a substantial cost saving in terms of hospital resources.

Prior to this point a number of well documented attempts over a long time period have been made to find a solid form of arsenic trioxide which could be delivered orally. The use of salt and/or particle micronisation, wetting or surfactant agents, strong dispersants such as citric acid and other approaches were all trialled unsuccessfully.

A further deterrent to the use of a solid oral form of arsenic trioxide is that to achieve acceptable bioavailability the arsenic trioxide must be dissolved within the stomach in less than about 20 minutes and preferably less than about 10 minutes. This is because the absorption of the arsenic III ion of arsenic trioxide occurs in the distal part of the small intestine and gastric emptying, on a stomach containing about 250 mL of liquid, occurs in a little over 23 minutes. The pH of the gastric juices on an empty stomach would be approximately pH 1 to 2 and so is strongly acidic. On discharge to the distal small intestine the pH increases to >pH6 and thus dissolution of any undissolved solid salt may be slow or retarded.

This means that any oral delivery form of arsenic trioxide must be soluble at pH 1 to 2 within a maximum time frame of 20 minutes, preferably significantly less, to ensure complete delivery of the solubilised arsenic trioxide dose in a timely and predictable manner. This dissolution time frame cannot be met with the use of solid arsenic trioxide which is only slightly soluble at neutral pH and while it is considered to be more soluble at acid pH, has been found to be still a very slow process even in vitro with strong stirring at low pH (see later experimental section). However, the inventor's realisation that a dried down arsenic carbonate and/or bicarbonate would completely dissolve in gastric juices within the 20 minute timeframe has allowed this challenge to be successfully addressed while still delivering the desired active arsenic three cation which is that delivered via the IV route. Even more surprising is that, in one embodiment, complete dissolution in gastric juices has been shown to occur in less than 30 seconds. This extremely short timeframe cannot be attained even with solid salt forms of the soluble meta salts of arsenic such as sodium or potassium meta arsenites.

Importantly, the strongly alkaline nature of the arsenic (III) carbonate or bicarbonate salt causes a very rapid bubbling and turbulent effervescence causing dissolution of the powder and dispersal of the salt, as the arsenic (III) cation, in the acid of the gastric fluid. The reaction is very fast, as is shown in the experimental section. Importantly, when compared to a salt like sodium meta arsenite, which will also dissolve although more slowly as shown in the experimental section, the strong acid/strong alkali reaction causes a turbulent fizzing and bubbling effect which effervescence assists in mixing the arsenic ion in the gastric fluid.

Further to the above, the arsenic carbonate and/or bicarbonate salt in an orally deliverable composition has two key advantages over other arsenic salts, such as sodium meta arsenite, including: (i) significantly faster dissolution in the acidic conditions of the stomach (or even at neutral pH); and (ii) the explosive, bubbling effervescence of the highly alkaline but solid arsenic carbonate and/or bicarbonate causes rapid mixing and dispersion in the stomach. The effervescence is a key feature as its effects mean an advantageous admixture in the stomach which then empties rapidly into the distal small intestine where the higher pH environment will limit solubility if the arsenic salt has not been satisfactorily dissolved and mixed. The resultant mixture in the body is the active arsenic III cation, a sodium cation (if a sodium salt is employed), carbon dioxide and carbonic acid, all of which mimic the effect of receiving an alkali pre-dissolved arsenic trioxide injection. In essence this means the arsenic III cation dose provided by the method of the present invention is the same as if the patient was given an equivalent IV dose of arsenic trioxide and so the therapeutic effect on cancers and other disease processes is predictable based on the already known efficacy of arsenic trioxide treatment.

In this patent specification, adjectives such as first and second, left and right, front and back, top and bottom, etc., are used solely to define one element or method step from another element or method step without necessarily requiring a specific relative position or sequence that is described by the adjectives.

Unless defined otherwise, all technical and scientific terms used herein have the same meaning as would be commonly understood by those of ordinary skill in the art to which this invention belongs.

The term "dispersant" as used herein, refers to an agent which improves the separation of particles of the arsenic carbonate or bicarbonate from one another and thereby aids in improving the speed of dissolution of that salt in the stomach juices of a patient.

The term "treatment", as used herein in relation to the various cancers treated by the arsenic carbonate or bicarbonate, means that the disease and the symptoms associated with the disease are alleviated, reduced, cured, or placed in a state of remission.

According to a first aspect of the invention, there is provided a pharmaceutical composition comprising an arsenic carbonate and/or bicarbonate and a pharmaceutically acceptable excipient.

Suitably, the pharmaceutical composition comprises the arsenic carbonate and/or bicarbonate in solid form.

Preferably, the arsenic carbonate and/or bicarbonate is an arsenic (III) carbonate or bicarbonate.

In certain embodiments the arsenic carbonate and/or bicarbonate may be an alkali metal and/or an alkaline earth metal arsenic carbonate and/or bicarbonate. In one preferred embodiment the arsenic carbonate and/or bicarbonate may be selected from the group consisting of a sodium arsenic carbonate and/or bicarbonate, a potassium arsenic carbonate and/or bicarbonate and a calcium arsenic carbonate and/or bicarbonate.

Preferably, the arsenic carbonate and/or bicarbonate is a sodium arsenic carbonate and/or bicarbonate and more preferably a sodium arsenic (III) carbonate or bicarbonate.

The arsenic carbonate and/or bicarbonate ions which may form part of the arsenic carbonate and/or bicarbonate salt are $As(CO_3)_2^-$, $As(CO_3)(OH)_2^-$, $As(CO_3)_2(OH)^{2-}$, and $As(CO_3)^+ As(OH)_2 CO^{3-}$ and $As(OH)_3(HCO^{3-})_2$.

These may be combined with a counter ion which may be selected from sodium, potassium, calcium and ammonium.

In one embodiment, the arsenic (III) carbonate or bicarbonate may be selected from the group consisting of NaAs(OH)$_2$CO$_3$, As$_2$(CO$_3$)$_3$, As(HCO$_3$)$_3$, Na$_2$As(OH)$_3$CO$_3$, NaAs(CO$_3$)$_2$, Na$_3$As(CO$_3$)$_3$, NaAs(HCO$_3$)$_4$, Na$_2$As(HCO$_3$)$_5$, Na$_3$As(HCO$_3$)$_6$ and closely related analogues wherein the sodium in the formulae presented is replaced with another counter ion.

The counter ion may be selected from sodium, potassium, calcium and ammonium.

The arsenic carbonate and/or bicarbonate may be a salt formed by dissolution of arsenic trioxide in a solution of a hydroxide of an alkali metal and/or an alkaline earth metal and reacted with a carbonate or bicarbonate compound. Arsenic trioxide is known to only be soluble in aqueous solutions at high pH, for example above about pH 12, and so only solutions of strong bases such as those formed by hydroxides of alkali metals and/or alkaline earth metals are likely to be suitable. However, potentially any strong base, for example ammonium hydroxide, may be used to dissolve the arsenic trioxide and thus may be suitable.

In one embodiment the hydroxide of an alkali metal and/or an alkaline earth metal may be selected from the group consisting of sodium hydroxide, potassium hydroxide, magnesium hydroxide, calcium hydroxide, lithium hydroxide, rubidium hydroxide, strontium hydroxide, barium hydroxide, and caesium hydroxide. These hydroxides are all known to form strongly basic aqueous solutions. Due to the nature of the counter ion some of these hydroxides may be less favoured than others. For example, some lithium salts may be physiologically less preferred. The use of sodium hydroxide to form the strongly basic solution in which the arsenic trioxide is dissolved is particularly preferred due to the current clinical use of a pH adjusted solution of sodium hydroxide containing arsenic trioxide for IV delivery. This has shown that IV use of a sodium hydroxide solution of arsenic trioxide is both safe, within the known degrees of arsenic toxicity, and effective in treating cancers.

In another embodiment the hydroxide may be ammonium hydroxide.

The composition may further comprise a drying agent, a disintegrant or dispersant. The drying agent, disintegrant or dispersant may be effervescent. In one embodiment, the drying agent, disintegrant or dispersant is a bicarbonate and/or a carbonate. Suitably, the disintegrant or dispersant is selected from the group consisting of sodium bicarbonate, sodium carbonate, potassium carbonate, potassium bicarbonate, calcium carbonate, magnesium carbonate and magnesium bicarbonate.

The disintegrant or dispersant contributes to the fast dissolution of the arsenic carbonate and/or bicarbonate in the gastric juices. The use of an effervescent disintegrant or dispersant, such as the bicarbonates or carbonates of alkali metals or alkaline earth metals, is particularly effective upon contacting the gastric juices as there is an immediate and turbulent fizzing reaction which acts to effectively separate the particles of the arsenic carbonate and/or bicarbonate to put them into solubilised ionic form.

The composition may be in the form of a tablet, suppository, granule or capsule. Any pharmacologically acceptable vehicle for the arsenic carbonate and/or bicarbonate may be acceptable so long as it does not interact with the arsenic carbonate and/or bicarbonate and does not impede the dissolution in the stomach. Capsules which are currently used for the delivery of actives to the stomach for rapid dissolution are considered particularly appropriate for use with the present composition, not least as the patient or medical staff will not come into direct contact with the arsenic compound during handling. The composition may be in the form of a powder or granules within the tablet or capsule. Depending on the method of drying down of the solvent to form the arsenic carbonate and/or bicarbonate, crystalline salts may even be provided. The solid formed may then be further pulverised or micronized or other such physical treatment to reduce the particle size if required to provide even faster dissolution.

The excipient may be any appropriate pharmaceutically acceptable excipient.

In one embodiment, the drying agent, disintegrant and the excipient may be one and the same.

According to a second aspect of the invention there is provided a method of treating a cancer in a patient including the step of orally administering an arsenic carbonate and/or bicarbonate to the patient to thereby treat the cancer.

A third aspect of the invention resides in an arsenic carbonate and/or bicarbonate for use in treating a cancer in a patient.

In certain embodiments of the second and third aspects, the arsenic carbonate and/or bicarbonate is administered in solid form.

In relation to the second and third aspects, in one embodiment the cancer is a haematological malignancy. In one embodiment the cancer is a leukaemia, multiple myeloma, a solid tumour or a lymphoma.

The cancer may be selected from the group consisting of squamous cell carcinoma, basal cell carcinoma, melanoma tumours of the epithelial lining of glands or ducts, adenocarcinoma, papillary carcinoma, papillary adenocarcinoma tumours of the liver and biliary tract, epatocellular carcinoma tumours of the gastrointestinal tract, squamous cell carcinoma of the esophagus, adenocarcinoma of the esophagus, colorectal carcinoma (colon cancer), gastric carcinoma (stomach cancer) tumours of the respiratory tract, bronchogenic carcinoma, small cell carcinoma, large cell carcinoma tumours of the urogenital tract, transitional cell carcinomas of the bladder, squamous cell carcinoma of the bladder, carcinoma of the prostate, carcinoma of the cervix, blood cells and related cells (leukemias), acute and chronic lymphocytic leukaemia, polycythemia vera, cancers of lymphoid tissue, malignant lymphomas including Hodgkin's lymphoma and non-Hodgkin's lymphoma, follicular lymphoma, diffuse lymphoma, small lymphocytic lymphoma, large cell lymphoma, lymphoblastic lymphoma, multiple myeloma, tumours of connective tissue, cancers of bone osteosarcoma, tumours of the nervous system, neuroblastoma, retinoblastoma, glioblastoma, oligodendroglioma tumours associated with oncogenic viruses, burkitts lymphoma, b cell lymphoma's in immuno-comprised individuals, nasopharyngeal carcinoma and hepatitis b virus hepatocellular carcinoma.

When the cancer is leukaemia it may be a form selected from the group consisting of acute lymphoblastic leukaemia (ALL), acute lymphoblastic B-cell leukaemia, acute lymphoblastic T-cell leukaemia, acute myeloblastic leukaemia (AML), acute promyelocytic leukaemia (APL), acute monoblastic leukaemia, acute erythroleukemic leukaemia, acute megakaryoblastic leukaemia, acute myelomonocytic leukaemia, acute undifferentiated leukaemia, chronic myelocytic leukaemia and chronic lymphocytic leukaemia.

Preferably, the cancer is acute promyelocytic leukaemia (APL).

When the cancer is a solid tumour it may one or more of cancer of the digestive tract, oesophagus, liver, stomach, colon, skin, brain, bone, breast, lung and soft tissues, including but not limited to various sarcomas and prostate cancer.

The cancer may be any cancer which is currently indicated for treatment by clinically available arsenic trioxide solutions or against which solutions of arsenic trioxide have been shown to demonstrate efficacy. In one embodiment, the lymphoma, leukaemia or solid tumour in the patient is refractory to standard methods of treatment, or is a relapsed case of leukaemia.

The arsenic carbonate and/or bicarbonate may be used alone or in combination with a further anti-cancer agent including wide range of known therapeutic agents such as, for example, immunotherapeutics, monoclonal antibodies, chemotherapeutics, radioprotectants and radiotherapeutics. Particularly, the oral delivery of the arsenic carbonate and/or bicarbonate may occur before, during or after the administration of one or more known antitumor agents including but not limited to mustard compounds, nitrogen mustard, chlorambucil, melphalan, cyclophosphamide, 6-mercaptopurine, 6-thioguanine, cytarabine, 5-fluorouracil, floxuridine, methotrexate, vincristine, vinblastine, taxol, etoposide, temiposide, dactinomycin, daunorubicin, doxorubicin, bleomycin, mitomycin, cisplatin, carboplatin, estramustine phosphate, hydroxyurea, BCNU, procarbazine, VM-26, interferons, and all-trans retinoic acid (ATRA), or other retinoids.

The therapeutic dose and dosing frequency of the arsenic carbonate and/or bicarbonate in the treatment of various cancers will depend on the nature of the cancer, the severity of the condition as well as age, body weight, condition and response of the individual patient. Importantly, such dosing can conveniently be decided upon based on standard processes and following the guidelines of current dosing regimes for IV delivery of arsenic trioxide. This is based upon the understanding that the present use of an arsenic carbonate and/or bicarbonate is effectively a more advantageous means by which to provide, to a patient, a therapeutic bioequivalence of arsenic trioxide and the active species derived therefrom in the body. The therapeutic effect obtained and therefore efficacy of the treatment will be substantially as is observed for treatment of cancers using arsenic trioxide. Studies on the use and activity of arsenic trioxide in treating a range of cancers are freely available in the scientific and medical literature. Thus, for specific cancers, the already developed dosing and toxicity protocols for clinically available arsenic trioxide by IV delivery can be used. In one embodiment, a daily dose of between 0.05 to 5.0 mg/kg/day may be suitable for delivery to a patient requiring induction therapy. A preferred dose may be about 0.15 mg/kg/day.

The patient being treated for the cancer will be a human in need of such arsenic trioxide therapy.

The arsenic carbonate and/or bicarbonate, of the second and third aspects, is as described for the first aspect. The arsenic carbonate and/or bicarbonate may be administered as part of the pharmaceutical composition of the first aspect. Preferably, the arsenic carbonate and/or bicarbonate is a dried down carbonate or bicarbonate salt of arsenic trioxide in sodium hydroxide solution with added amounts of sodium bicarbonate and/or sodium carbonate. This solid composition can then be taken orally by the patient, preferably in the form of a capsule or tablet containing the composition.

According to a fourth aspect of the invention there is provided a process for producing an arsenic carbonate and/or bicarbonate in solid form for oral delivery to a patient in need of cancer therapy including the steps of:
  (a) solubilising arsenic trioxide in a strongly basic solution;
  (b) contacting the strongly basic solution with a carbonate and/or bicarbonate compound; and
  (c) removing the solvent from the strongly basic solution containing the dissolved arsenic carbonate and/or bicarbonate compound;
to thereby produce the arsenic carbonate and/or bicarbonate in solid form.

The strongly basic solution may be a solution of at least pH 9, better still at least pH 10, preferably at least pH 11, more preferably at least pH 12 and even more preferably at about pH 13 or above.

The strongly basic solution may be a solution of a hydroxide of an alkali metal and/or an alkaline earth metal or ammonium hydroxide.

In one embodiment the hydroxide of an alkali metal and/or an alkaline earth metal may be selected from the group consisting of sodium hydroxide, potassium hydroxide, magnesium hydroxide, calcium hydroxide, lithium hydroxide, rubidium hydroxide, strontium hydroxide, barium hydroxide and caesium hydroxide. The hydroxide of an alkali metal and/or an alkaline earth metal and the arsenic carbonate and/or bicarbonate formed therefrom may be as described for the first aspect.

In one embodiment, the strongly basic solution is an aqueous solution. In one highly preferred embodiment, the strongly basic solution is an aqueous potassium hydroxide solution.

In one embodiment, the strongly basic solution is an aqueous solution. In one highly preferred embodiment, the strongly basic solution is an aqueous sodium hydroxide solution of pH about 13.

The solvent may be removed by evaporation under heat and/or reduced pressure. The removal of water, as the solvent, can be carried out using a range of standard apparatus which are available to the skilled addressee. The use of a vacuum oven may be particularly appropriate.

Attempts should be made to dissolve the arsenic trioxide in a minimal amount of aqueous basic solution to thereby minimise the time required for subsequent removal of the water.

The arsenic carbonate and/or bicarbonate may be as described for the first aspect. Particularly, the arsenic carbonate and/or bicarbonate may be an arsenic III carbonate and/or bicarbonate.

The contacting step contemplates the situations wherein (i) the arsenic trioxide and carbonate or bicarbonate compound are mixed prior to the addition of the strongly basic solution; or (ii) where the strongly basic solution and the carbonate or bicarbonate compound are mixed prior to addition of the arsenic trioxide; and (iii) where the arsenic trioxide and strongly basic solution are mixed prior to addition of the carbonate or bicarbonate compound.

Suitably, the carbonate or bicarbonate compound will have a high solubility in water to minimise the volume of water required for a batch. The carbonate and bicarbonate may be selected, appropriately, from the group consisting of sodium bicarbonate, sodium carbonate, potassium carbonate, potassium bicarbonate, calcium carbonate and magnesium carbonate.

In certain embodiments a drying agent, dispersant or disintegrant may be added to the arsenic carbonate and/or bicarbonate in solid form after the solvent has been removed. This may be instead of or in addition to the carbonate or bicarbonate compound added to the strongly basic solution. This may be a useful approach when it is desired to use a dispersant or disintegrant which has a high capacity for holding onto water. This may mean that it is difficult to dry the solid composition after removal of the water and a wet solid or paste may result which, while still effective biologically, is more difficult to manipulate into a tablet or capsule form.

In one preferred embodiment, sodium bicarbonate is added to the strongly basic solution along with the arsenic trioxide and the solvent then removed. Sodium carbonate is then added to the dried arsenic carbonate and intimately mixed via simple mechanical mixing or grinding or the like to achieve better drying and allow for easier handling. This provides for a composition which dries down readily from the basic aqueous solution but which also contains a very effective dispersant system due to the presence of both sodium bicarbonate and carbonate.

Sodium carbonate may be added in an amount of between 0.1% to 15% of the final weight of the composition, preferably between 2 to 12%, more preferably between about 5% to 9%.

The final arsenic carbonate containing powder which is produced by use of any one or more of the above embodiments can be milled and mixed with standard capsule or tablet excipients for the production of an oral delivery form of the drug. The dried and milled arsenic carbonate and/or bicarbonate is then at a very high pH (about pH12) which on exposure to the low pH of the chyme (pH1 without food) results in a very strong fizzing turbulent reaction between the very acidic chyme and the very alkaline arsenic carbonate or bicarbonate composition to cause very rapid dissolution and dispersion of the solid composition.

A fifth aspect of the invention resides in an arsenic carbonate and/or bicarbonate in solid form when produced by the process of the fourth aspect.

A sixth aspect of the invention resides in a method of delivering a therapeutically effective amount of arsenic to a patient including the step of administering to the patient an appropriate amount of an arsenic carbonate and/or bicarbonate.

Suitably, the administration is oral administration of a solid form of arsenic carbonate and/or bicarbonate.

The method of the sixth aspect may be performed in keeping with any of the embodiments described for the first to the fifth aspects.

EXPERIMENTAL

Characterisation and Comparison Experiments of the Dissolution of Arsenic Salts

The literature describes the low solubility of arsenic trioxide. This is variously given as between 1.2 gm to 3.7 gm/100 mL at 20° C. but it is more soluble at low pH, especially in hydrochloric acid, while being reasonably soluble at high pH. Given this, it is naturally assumed that if an amount of arsenic trioxide, preferably milled to a small and consistent particle size, was dispersed into a low pH solution (with or without stirring) and aided with suitable known dispersants, rapid dissolution would be achieved. Following this logic, a considerable number of experiments were conducted with differing formulations in capsules exposed to artificial stomach solutions with surprisingly poor results and very slow dissolution. It was concluded that it was not possible to achieve any reasonable level of dissolution of arsenic trioxide at low pH (i.e. in the simulated physiological conditions of the stomach) compared with that which may be achieved in a strong alkaline solution. These arsenic trioxide dissolution experiments are set out below.

Experiment 1

Dissolution of 1 mg Capsule of Arsenic Trioxide
Composition of Capsule Used in Dissolution Testing:

| RX500950.01 | mg | % | g |
|---|---|---|---|
| Arsenic Trioxide (Sigma Aldrich) | 1.0 | 0.71% | 2.14 |
| Lactose Monohydrate (Supertab 30GR) | 110.0 | 78.57% | 235.71 |

-continued

| RX500950.01 | mg | % | g |
|---|---|---|---|
| Citric Acid Anhydrous | 13.4 | 9.57% | 28.71 |
| Crospovidone (Kollidon CL) | 7.3 | 5.21% | 15.64 |
| Poloxamer 188 m (*Kolliphor P188m) | 7.3 | 5.21% | 15.64 |
| Magnesium Stearate | 1.0 | 0.71% | 2.14 |
| Total | 140.0 | 100.00% | 300.0 |
| Hard Gelatin Capsule (Size 4 White) | ~38 mg | | 2143 |

Note:
Kolliphor P188m was previously known as Lutrol m68

To manufacture the components for insertion into the capsule all ingredients were sieved through a 500 μm sieve into a sealable jar and blended for 20 minutes in a tumble blender. The blended powder was filled into the Size 4 white hard gelatin capsules at a fill weight of 140 mg.

For the dissolution experiments the medium was 0.1M HCl and purified water with a volume of 500 ml also containing 0.5% benzalkonium chloride (BKC) at 37° C. The paddle stir speed was 50 rpm. The capsule shell disrupted within three minutes and all contents were expelled in less than five minutes. Only 5% arsenic trioxide was dissolved after 20 minutes. Even after 19 hours only 60% was dissolved. The presence of the citric acid reduced the pH of the medium from ~8.0 to ~7.3. Given the anticipated increase in solubility at a higher pH, these experiments were repeated at a higher pH as indicated in the tables below wherein the mean and range values represented percentage dissolution of the arsenic trioxide.

1 mg Batch (50 rpm)—pH 8 Buffer with 0.5% BKC

| Time (minutes) | Mean | Range |
|---|---|---|
| 5 | 4 | 3-6 |
| 10 | 13 | 7-17 |
| 20 | 35 | 22-38 |
| 30 | 52 | 41-68 |
| T = ∞ | 82 | 66-100 |

5 mg Batch (100 rpm)—pH 8 Buffer with 0.5% BKC

| Time (minutes) | Mean | Range |
|---|---|---|
| 10 | 18 | 10-25 |
| 20 | 44 | 26-59 |
| 30 | 63 | 47-80 |
| 40 | 76 | 55-92 |

As was expected, at higher pH more of the salt was dissolved at 20 minutes, being the time dissolution should ideally be achieved by in the stomach, (range 22-38% for the 1 mg capsule and 26-59% for a 5 mg capsule) however these values are all well below a complete dissolution level and this higher pH would not be expected in the chyme on an empty stomach A further dissolution experiment was conducted in a solution of 0.1M NaOH (pH 13) and, as expected, more arsenic trioxide could be dissolved with a 100% level reached between 15-20 minutes as indicated in the table below.

| % Recovered (weight Corrected) | |
| --- | --- |
| Time (minutes) | Mean |
| 5 | 12 |
| 10 | 65 |
| 15 | 96 |
| 20 | 109 |
| 25 | 116 |
| 30 | 114 |

However, even in this non physiological solution the time taken to reach a high dissolution level was still a little longer than would ideally be required for a complete dissolution in the stomach chyme. Thus a different approach was needed to produce a high level of solubility for an arsenic three salt in stomach acid conditions. Alternate arsenic three salts, especially the meta arsenite will dissolve readily in neutral solutions and at low pH. Experiments showed that sodium meta arsenite (As3+, Sigma Aldrich 96% pure) will dissolve in less than 2 minutes at pH 7 and in less than one minute at pH 1-2 (see below), however, the present invention provides a new and unique solution with the creation of an alternative even faster dissolving arsenic carbonate or bicarbonate salt which has the added advantage of being able to be simply made and where the capsule ingredients create a turbulent fizzing and mixing effect, ensuring greater blending of the capsule contents rapidly in the stomach chyme. Such a salt of the invention was created as described in trial 3 (below) and is referred to hereinafter as AC01.

Three samples were analysed as described below. Two known salts of arsenic where selected as both are considered to be highly soluble as comparators. One purchased sample was commercial sodium meta arsenite (Sigma-Aldrich purity>96%) the second was arsenic trioxide (Sigma-Aldrich). The third sample tested was the AC01 sample of the invention. The three solid samples were first analysed by ICPMS for carbon. Each of sodium meta arsenite and arsenic trioxide gave <0.1% C while the AC01 sample gave 5.25% C. The AC01 sample was then analysed for H and gave 1.32%, for As it gave 14.1% and for Na it gave 30.2%.

The AC01 sample was then examined by X-ray photoelectron spectroscopy (XPS) and was shown to contain arsenic as $As^{3+}$, C as carbonate, Na, and O as hydroxide and as carbonate. XPS scans of the AC01 sample are shown in FIGS. 1 and 2. Atom % ratios were measured to give: O 1s—42.42; C 1s—24.67; Na 1s—19.72; and As 3d—13.20. The As 3d5/2 binding energy of 43.93 eV is consistent with an AS (III) oxidation state. The C1S shows the presence of carbonate and it is well documented that the surface of carbonates very easily contaminates with hydrocarbons from the air, explaining the observed impurity. The atomic concentration does not include hydrogen. XPS therefore indicates a trivalent arsenic atom in the RD samples with a binding energy that is different from either arsenic trioxide (the starting material) or sodium meta arsenite (the compound formed when arsenic trioxide is dissolved in sodium hydroxide).

The carbon content of the AC01 sample suggested either of two arsenic carbonate complexes: $NaAs(OH)_2CO_3$ where As is trivalent; and $NaAs(OH)_3(HCO_3)_2$ where As is pentavalent. The ICPMS for carbon is closer to the calculated level for the trivalent compound, as shown in the table below, and the XPS analytical data, as discussed above, confirms it is $NaAs(OH)_2CO_3$ comprising the As (III) species.

| Element | ICPMS results | Calculated - AsIII | Calculated - AsV |
| --- | --- | --- | --- |
| C | 5.25 | 6.25 | 8.86 |
| As | 14.1 | 39.1 | 27.7 |
| Na | 30.2 | 11.98 | 8.49 |

Infra-red spectroscopy was also performed on the $NaAs(OH)_2CO_3$ formed by a process of the invention. These scans were quite different to those obtained from sodium meta arsenite. The main difference is the presence of a large carbonyl peak at $1400 \text{ cm}^{-1}$ that is expected to be due to the carbonyl bond in the carbonate group. The conclusion from the IR data is that the compound is definitively not a sodium meta arsenite.

Mass Spectrometry was performed on sample of arsenic trioxide, sodium meta arsenite and the $NaAs(OH)_2CO_3$ formed by the process of the invention. The characteristic peaks for the $NaAs(OH)_2CO_3$ formed by the process of the invention were found at 64, 74, 129 and 229. It was notable that none of these peaks are present in the spectra of arsenic trioxide or sodium meta arsenite thereby further confirming that the arsenic carbonate salt of the invention is indeed a unique structure and not simply arsenic trioxide or sodium meta arsenite.

The arseno carbonate of the present invention tested in IR, mass spec and XPS was formed by two different approaches as set out below. Each yielded essentially the same characterisation data and so are presumed to provide the same product:

Method A
1. 50 ml of 0.5M NaOH was prepared by dissolving 1 gm of NaOH in 50 ml of water.
2. To 25 ml of 0.5M NaOH was added 250 mg arsenic trioxide and this was dissolved with sonication.
3. 625 mg of sodium carbonate was added to this solution.
4. The mixture was stirred at 60° C. until the water had evaporated.

Method B
1. 50 ml of 0.5M NaOH was prepared by dissolving 1 gm of NaOH in 50 ml of water.
2. To 25 ml of 0.5M NaOH was added 250 mg arsenic trioxide and this was dissolved with sonication.
3. 625 mg of sodium carbonate was added to this solution.
4. The mixture was then frozen and placed on the freeze dryer to give a white powder.

Three test samples (sodium meta arsenite, arsenic trioxide and AC01) were tested in dissolution studies wherein each sample salt was added to 100 mL of pure water, with stirring, at room temperature with the results shown in the table below.

| Arsenic salt form | Dissolution Time at pH 7 | Dissolution Time at pH 1-2 |
| --- | --- | --- |
| Arsenic trioxide | Not dissolved in 3 hours | Not dissolved in 3 hours |
| Sodium meta arsenite | 1 minute 40 seconds - Final pH after dissolution = 10.2 | 55 seconds - Final pH after dissolution = 1.27 |
| AC01 (Sodium arsenic carbonate) | 40 seconds - Final pH after dissolution = pH 8.95 | <5-10 seconds - Final pH after dissolution = 1.13 |

The following results demonstrate that the concept of the formation of a strongly alkaline arsenic carbonate or bicarbonate compound of the invention will give dissolution within 1 minute in solution even at neutral pH and even faster at acidic pH.

Trial 1—Test Dissolution of Arsenic Trioxide Solely in Sodium Bicarbonate

Approximate Final formulation (based on an estimated 250 mg Capsule):
Arsenic Trioxide 5 mg
Sodium Bicarbonate 245 mg (Solubility Sodium Bicarbonate 9 g/100 ml pH 0.1M solution=8.3)

2540 mg of Sodium Bicarbonate was dissolved in approximately 27.2 mls water (dissolved in less than 5 minutes). 50 mg Arsenic Trioxide was then added to this bicarbonate solution. The Arsenic Trioxide would not dissolve even with heating indicating a strongly basic solution is required and even then the salt would not dissolve in this Sodium Bicarbonate solution alone.

Trial 2—Preparation of a Sodium Arsenic Carbonate of the Invention Using NaOH with Sodium Bicarbonate Approximate Final formulation (based on an estimated 250 mg Capsule):
Arsenic Trioxide 5 mg
Sodium Bicarbonate 245 mg Arsenic Trioxide (50 mg) was dissolved with low heat in 27 mL of 0.5M NaOH. 2450 mg Sodium Bicarbonate was added and dissolved. The water was evaporated off at 72/74° C. ~1 hr 30 minutes. The resultant powder was added to a #3 capsule shell (shell weight 45.7 mg, powder weight 209 mg). The dissolution of this capsule was then tested in simulated gastric juices.

Dissolution in Simulated Gastric Solution

Simulated gastric solution was made up containing—2 g NaCl, 7 ml of 37% HCl and then made up to 1 L—pH 1.2 with water. The capsule containing the sodium arsenic carbonate made as described for trial 2 above, was added to 150 mL of the simulated gastric solution and stirred at 37° C. In less than one minute the capsule shell had dissolved and in less than 2 minutes the arsenic carbonate contents had completely dissolved with a slight $CO_2$ effervescence. It was noted however that the powder was difficult to dry meaning handling and weighing out was challenging and it was felt that, potentially, bicarbonate may be converting to carbonate at temperatures over 50° C. (Bicarbonate->Carbonate+$CO_2$+$H_2O$).

Trial 3—Preparation of AC01 (Sodium Arsenic Carbonate) Using NaOH, Sodium Carbonate at 5% to Precipitate, Sodium Bicarbonate Dry-Blended Sodium bicarbonate can be difficult to dry on its own due to the potential for conversion to sodium carbonate, $CO_2$ and water above 50° C. Hence, experiments were conducted using the more stable sodium carbonate from 1% up to a level of 10%. Since sodium carbonate is more soluble than bicarbonate it was felt it may be faster to evaporate off due to the smaller volume required.

Approximate Final formulation:
Arsenic Trioxide 5 mg
Sodium Carbonate 12.5 mg (5% on an estimated 250 mg capsule)
Sodium Bicarbonate 232.5 mg 100 mg of arsenic trioxide was dissolved in 10 mL of 0.5M NaOH with heat (<ten minutes). 250 mg Sodium Carbonate was then added (dissolves almost straight away) and excess water evaporated. When dry, for every 17.5 mg (5 mg Arsenic Trioxide+12.5 mg sodium carbonate) 232.5 mg sodium bicarbonate was added, and the dry blend ground to reduce the particle size with a mortar and pestle. 3 capsules were then packed with 263 mg, 251 mg and 261 mg of the manufactured AC01 powder.

Dissolution experiments were then carried out on the AC01 at 3 different pH levels. Firstly simulated gastric fluid (pH 1.24) was used, then a solution at pH 4.5 and then a neutral solution at pH 7.0. Prior to addition of the capsules 150 mls of the dissolution solution was heated to 37° C. and the solution contained a spin bar at a speed of 2. The appropriate capsule was then added.

It was found that in less than two minutes, in all three dissolution mediums, the AC01 powder was dissolved. It was notable that there is less $CO_2$ produced at a pH of 4.5 and 7. The capsule shell itself was also less dissolved at pH's 4.5 and 7 but was completely empty in each case. Similar experiments performed with 1% and 2.5% and 10%, in formation of the AC01 salt as described above, sodium carbonate yielded similar dissolution results.

Further Approach to Compound and Tablet Formation

The bulk formula is provided below for a series of different strength tablets with the amounts given relating to production of a 1000 capsule batch.

10 mg Active Capsule:
10 g Arsenic Trioxide
*10 g Water
4 g NaOH
25 g Sodium Carbonate
221 g Sodium BiCarbonate.
This provides for a 260 mg fill.
5 mg Active Capsule:
5 g Arsenic Trioxide
*10 g Water
4 g NaOH
25 g Sodium Carbonate
231 g Sodium BiCarbonate.
This gives a 265 mg fill.
1 mg Active Capsule:
1 g Arsenic Trioxide
*10 g Water
4 g NaOH
25 g Sodium Carbonate
240 g Sodium BiCarbonate.
This gives a 270 mg fill.
* Water is dried off and does not form part of the final formulation.

The manufacturing procedure is as follows for all strength capsules. Dispensed Arsenic trioxide and Sodium hydroxide are placed in a suitable vessel. The dispensed water is added on top. The materials are mixed by swirling. Caution is required at this point as the solution gets hot. Once the Arsenic trioxide and Sodium Hydroxide have fully dissolved, add the dispensed Sodium Carbonate. Ensure the Sodium carbonate is fully wetted. For the 10 mg and 5 mg preparation a stiff slurry is formed, the 1 mg forms a semi solid. The mixtures are then left to cool to room temperature over 4-24 hrs.

Next, carefully add the preparations to the dispensed Sodium Bicarbonate. Use some of the bicarbonate to "wash" all of the slurry out and then thoroughly incorporate the slurry into the Bicarbonate. Pass the mix through a screen of 1.5-2.0 mm mesh size. To ensure the screen is unblended and clear this step may be performed more than once. Typically, a 98% yield at this point will be observed and usually passing the material through twice using a 1.7 mm sieve is sufficient. The aim is to achieve a free flowing granular material.

The material is then spread out on a tray and placed in a vacuum oven, set at 40-45° C., and dried under vacuum (pump running constantly) for 6-24 hrs. When calculating the loss on drying a theoretical moisture level of about 2% should be apparent. The dried material is then passed through a 500 um sieve with the material being passed through several times until the sieve is effectively washed clear. The material is then blended in a turbular type blender (10 minutes at 30 rpm) and will then be ready to be filled into the capsules. This approach has been found to provide for an appropriately dry and free flowing material which lends itself to easy capsule filling subsequently.

One advantage of the present invention lies in ensuring both very rapid and complete dissolution of the arsenic carbonate and/or bicarbonate (preferably arsenic III form) in the stomach contents (chyme), which has a pH of about 1 in resting mode without food. This will ensure that the salt will form an arsenous acid and be readily available for absorption in the small intestine. If this rapid dissolution does not occur and the stomach contents pass into the small intestine, which has a pH of about 6, it is unlikely that the arsenic salt will dissolve and a proportion will therefore pass through to the faeces. The key in treating cancer patients with a solid oral delivery form is to have the bioequivalence over a 24 hour period be approximately the same as that of the liquid injection form. Any failure to obtain complete dissolution in the stomach will mean that this aim is not achieved. The present invention provides an arsenic carbonate and/or bicarbonate salt which satisfies this requirement in a surprisingly effective manner.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

The invention claimed is:

1. A pharmaceutical composition comprising an effective amount of arsenic carbonate and/or arsenic bicarbonate and a pharmaceutically acceptable excipient.

2. The composition of claim 1 wherein the pharmaceutical composition comprises the arsenic carbonate and/or bicarbonate in solid form.

3. The composition of claim 1 wherein the arsenic carbonate and/or bicarbonate is an arsenic (III) carbonate or bicarbonate.

4. The composition of claim 1 wherein the arsenic carbonate and/or bicarbonate is an alkali metal and/or an alkaline earth metal arsenic carbonate and/or bicarbonate.

5. The composition of claim 1 wherein the arsenic carbonate and/or bicarbonate is selected from the group consisting of a sodium arsenic carbonate and/or bicarbonate, a potassium arsenic carbonate and/or bicarbonate and a calcium arsenic carbonate and/or bicarbonate.

6. The composition of claim 1 wherein the arsenic carbonate and/or bicarbonate comprises an ion forming part of an arsenic carbonate and/or bicarbonate salt selected from the group consisting of $As(CO_3)_2^-$, $As(CO_3)(OH)_2^-$, $As(CO_3)_2(OH)^{2-}$, and $As(CO_3)^+$ $As(OH)_2CO^{3-}$ and $As(OH)_3$ $(HCO^{3-})_2$.

7. The composition of claim 6 wherein the ion forming part of the arsenic carbonate and/or bicarbonate salt can be combined with a counter ion selected from the group consisting of sodium, potassium, calcium and ammonium.

8. The composition of claim 3 wherein the arsenic (III) carbonate or bicarbonate is selected from the group consisting of $NaAs(OH)_2CO_3$, $NaAs_2(CO_3)_3$, $As(HCO_3)_3$, $Na_2As(OH)_3CO_3$, $NaAs(CO_3)_2$, $Na_3As(CO_3)_3$, $NaAs(HCO_3)_4$, $Na_2As(HCO_3)_5$, $Na_3As(HCO_3)_6$ and closely related analogues wherein the sodium in the formulae is replaced with another counter ion.

9. The composition of claim 3 wherein the arsenic (III) carbonate or bicarbonate is $NaAs(OH)_2CO_3$.

10. The composition of claim 1 further comprising one or more of a drying agent, a disintegrant and a dispersant.

11. The composition of claim 10 wherein the disintegrant or dispersant is selected from the group consisting of sodium bicarbonate, sodium carbonate, potassium carbonate, potassium bicarbonate, calcium carbonate, magnesium carbonate and magnesium bicarbonate.

12. A method of treating a cancer in a patient including the step of orally administering a pharmaceutical composition comprising an effective amount of an arsenic carbonate and/or arsenic bicarbonate and a pharmaceutically acceptable excipient to the patient to thereby treat the cancer.

13. The method of claim 12 wherein the arsenic carbonate and/or bicarbonate is administered in solid form.

14. The method of claim 12 wherein the cancer is selected from a haematological malignancy, a solid tumour and a lymphoma.

15. The method of claim 14 wherein the cancer is selected from the group consisting of acute lymphoblastic leukaemia (ALL), acute lymphoblastic B-cell leukaemia, acute lymphoblastic T-cell leukaemia, acute myeloblastic leukaemia (AML), acute promyelocytic leukaemia (APL), acute monoblastic leukaemia, acute erythroleukemic leukaemia, acute megakaryoblastic leukaemia, acute myelomonocytic leukaemia, acute undifferentiated leukaemia, chronic myelocytic leukaemia and chronic lymphocytic leukaemia.

16. A process for producing a pharmaceutical composition comprising an effective amount of an arsenic carbonate and/or arsenic bicarbonate in solid form and a pharmaceutically acceptable excipient for oral delivery to a patient in need of cancer therapy including the steps of:
   (a) solubilizing arsenic trioxide in a strongly basic solution;
   (b) contacting the strongly basic solution with a carbonate and/or bicarbonate compound;
   (c) removing the solvent from the strongly basic solution containing dissolved arsenic carbonate and/or bicarbonate compound to produce the arsenic carbonate and/or bicarbonate in solid form; and
   (d) adding one or more of a drying agent, dispersant or disintegrant to the arsenic carbonate and/or bicarbonate in solid form after the solvent has been removed, to thereby produce the pharmaceutical composition comprising an effective amount of arsenic carbonate and/or bicarbonate in solid form and a pharmaceutically acceptable excipient.

17. The process of claim 16 wherein the strongly basic solution is a solution of at least pH 9.

18. A method of delivering a therapeutically effective amount of an arsenic ion to a patient comprising the step of administering to the patient a pharmaceutical composition comprising an effective amount of an arsenic carbonate and/or arsenic bicarbonate and a pharmaceutically acceptable excipient.

19. The method of claim 18 wherein the administration is oral administration of the pharmaceutical composition comprising a solid form of the arsenic carbonate and/or bicarbonate and a pharmaceutically acceptable excipient.

* * * * *

(12) SUPPLEMENTAL EXAMINATION CERTIFICATE

United States Patent
Eutick

(10) Number: US 10,493,099 F1
(45) Certificate Issued: Oct. 12, 2023

Control No.: 96/050,016
Primary Examiner: Ling X. Xu

Filing Date: Sep. 21, 2023

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 2009/0246291 | 10/2009 | Burger et al. |

FOREIGN PATENT DOCUMENTS

| | | |
|---|---|---|
| WO | 99/24029 | 5/1999 |
| WO | 2004/032822 | 4/2004 |
| WO | 2006/121280 | 11/2006 |
| WO | 2011/086193 | 7/2011 |

OTHER DOCUMENTS

Neuberger et al., Arsenic(III) Carbonate Complexing, Applied Geochemistry, 20 (2005) 1218-1225

Lee et al., Arsenic Carbonate Complexes in Aqueous Systems, Biogeochemistry of Environmentally Important Trace Elements, 835 (2002) 33-41

Swindell et al., Anticancer Activity of Small-Molecule and Nanoparticulate Arsenic(III) Complexes, Inorganic Chemistry, 52(21) (2013) 12292-12304

Ralph, Arsenic-Based Antineoplastic Drugs and Their Mechanisms of Action, Metal-Based Drugs, vol. 2008/260146 (2007) 1-13